US007432296B2

(12) United States Patent
Sundermann et al.

(10) Patent No.: US 7,432,296 B2
(45) Date of Patent: Oct. 7, 2008

(54) PHARMACEUTICAL FORMULATIONS CONTAINING SUBSTITUTED 2-ARYL-AMINOACETIC ACID COMPOUNDS AND/OR SUBSTITUTED 2-HETEROARYL-AMINOACETIC ACID COMPOUNDS

(75) Inventors: Bernd Sundermann, Aachen (DE); Michael Przewosny, Aachen (DE); Werner Englberger, Stolberg (DE); Klaus Schiene, Düsseldorf (DE)

(73) Assignee: Gruenenthal GmbH, Aachen (DE)

( * ) Notice: Subject to any disclaimer, the term of this patent is extended or adjusted under 35 U.S.C. 154(b) by 129 days.

(21) Appl. No.: 11/202,037

(22) Filed: Aug. 12, 2005

(65) Prior Publication Data
US 2006/0035959 A1 Feb. 16, 2006

Related U.S. Application Data

(63) Continuation of application No. PCT/EP2004/001062, filed on Feb. 5, 2004.

(30) Foreign Application Priority Data
Feb. 13, 2003 (DE) ................. 103 06 202

(51) Int. Cl.
A01N 43/22 (2006.01)
A01N 43/12 (2006.01)
A01N 43/00 (2006.01)
A61K 31/38 (2006.01)
A61K 31/385 (2006.01)
A61K 31/33 (2006.01)

(52) U.S. Cl. ................. 514/434; 514/443; 514/183
(58) Field of Classification Search .......... 514/434, 514/443, 183
See application file for complete search history.

(56) References Cited

U.S. PATENT DOCUMENTS

| 3,520,922 | A | | 7/1970 | Wagner |
| 4,223,039 | A | | 9/1980 | Rose et al. |
| 5,171,854 | A | * | 12/1992 | Schmidt et al. ............ 540/222 |
| 6,232,467 | B1 | | 5/2001 | Petasis et al. |
| 6,277,850 | B1 | | 8/2001 | Lubisch et al. |

FOREIGN PATENT DOCUMENTS

| EP | 0 054 812 A1 | 6/1982 |
| EP | 0 568 136 A1 | 11/1993 |
| EP | 0 807 621 A1 | 11/1997 |
| EP | 1 078 917 A | 2/2001 |
| JP | 53-015325 | 2/1978 |
| WO | WO 91/12002 A1 | 8/1991 |
| WO | WO 98/11073 A1 | 3/1998 |
| WO | WO 98/14427 A1 | 4/1998 |
| WO | WO 98/22493 | 5/1998 |
| WO | WO 98/42673 A1 | 10/1998 |
| WO | WO 00/24510 A1 | 5/2000 |
| WO | WO 00 35858 A1 | 6/2000 |
| WO | WO 01/55091 A1 | 8/2001 |
| WO | WO 01/58875 A2 | 8/2001 |
| WO | WO 01/90051 A1 | 11/2001 |
| WO | WO 02/09688 A1 | 2/2002 |
| WO | WO 02/44171 A1 | 6/2002 |
| WO | WO 03/059891 A1 | 7/2003 |

OTHER PUBLICATIONS

STIC search document (STIC_Search_07_08).*
International Search Report dated Sep. 4, 2004 (twelve (12) pages).
Bruce M. Baron, et al., "[³H]MDL 105,519, a High-Affinity Radioligand for the N-Methyl-D-aspartate Receptor-Associated Glycine Recognition Site", The Journal of Pharmacology and Experimental Therapeutics, (1996), pp. 62-68, vol. 279, copyright 1996, The American Society for Pharmacology and Experimental Therapeutics.
David Dubuisson, et al., "The Formalin Test: A Quantitative Study of the Analgesic Effects of Morphine, Meperidine, and Brain Stem Stimulation in Rats and Cats", Pain, (1977), pp. 161-174, vol. 4, Elsevier/North-Holland Biomedical Press.
Terrence J. Coderre, et al., "Contribution of Central Neuroplasticity to pathological Pain: Review of Clinical and Experimental Evidence", Pain, (1993), pp. 259-285, vol. 52, Elsevier Science Publishers B.V.
Nicos A Petasis, et al., "A New and Practical Synthesis of a-Amino Acids from Alkenyl Boronic Acids", J. Am. Chem. Soc., (1997), pp. 445-446, vol. 119.
Nicos A. Petasis, et al., "A New Synthesis of α-Arylglycines from Aryl Boronic Acids", Tetrahedron, (1997) pp. 16463-16470, vol. 53, No. 48, Elsevier Science Ltd., PII: S0040-4020(97)01028-4.
Gordon S. Currie, et al., "Chirally Templated Boronic Acid Mannich Reaction in the Synthesis of Optically Active a-Amino Acids", J. Chem. Soc., Perkin Trans., (2000), pp. 2982-2990, vol. 1, The Royal Society of Chemistry.
Nicos A. Petasis, et al., "One-Step Three-Component Reaction Among Organoboronic Acids, Amines and Salicylaldehydes", Tetrahedron Letters, (2001) pp. 539-542, vol. 42, Published by Elsevier Science Ltd.

* cited by examiner

Primary Examiner—Sreeni Padmanabhan
Assistant Examiner—Umamaheswari Ramachandra
(74) Attorney, Agent, or Firm—Crowell & Moring LLP

(57) ABSTRACT

Pharmaceutical formulations containing substituted 2-aryl-aminoacetic acid compounds and/or substituted 2-heteroaryl-aminoacetic acid compounds corresponding to formula I, as well as to their use in the production of drugs and in related methods of treating or inhibiting pain and neurodegenerative disease.

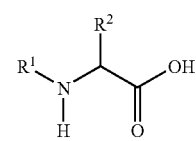

12 Claims, No Drawings

PHARMACEUTICAL FORMULATIONS CONTAINING SUBSTITUTED 2-ARYL-AMINOACETIC ACID COMPOUNDS AND/OR SUBSTITUTED 2-HETEROARYL-AMINOACETIC ACID COMPOUNDS

CROSS REFERENCE TO RELATED APPLICATIONS

This application is a continuation of International Patent Application No. PCT/EP2004/001062, filed Feb. 5, 2004, designating the United States of America, and published in German as WO 2004/071381 A2, the entire disclosure of which is incorporated herein by reference. Priority is claimed based on German Patent Application No. 103 06 202.5, filed Feb. 13, 2003.

FIELD OF THE INVENTION

The present invention relates to pharmaceutical preparations containing substituted 2-arylaminoacetic acid compounds and/or substituted 2-heteroarylaminoacetic acid compounds and the use thereof for the production of pharmaceutical preparations and in related methods of treatment.

BACKGROUND OF THE INVENTION

Pain is one of the basic clinical symptoms. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids, such as for example morphine, are effective in the treatment of severe to very severe pain, but they exhibit unwanted accompanying symptoms, such as for example respiratory depression, vomiting, sedation, constipation or the development of tolerance. Moreover, they are less effective in treating neuropathic or incidental pain, which is in particular experienced by tumour patients.

Opioids exert their analgesic effect by binding to membrane receptors belonging to the family of G protein-coupled receptors. There are moreover further receptors and ion channels which play a role in the system governing the genesis and transmission of pain, such as for example the N-methyl-D-aspartate (NMDA) ion channel, via which a substantial proportion of synaptic communication proceeds and by which calcium ion exchange between a neuronal cell and its surroundings is controlled.

Knowledge about the physiological significance of ion channel-selective substances has been obtained by the development of the patch-clamp technique with which the action of NMDA antagonists on the calcium balance in the cell's interior may be detected.

SUMMARY OF THE INVENTION

One object underlying the present invention was accordingly to provide novel pharmaceutical preparations which are in particular suitable for combatting pain, preferably chronic and/or neuropathic pain, and which preferably do not exhibit the undesired accompanying symptoms which occur with opioids or at least exhibit them to a reduced extent.

This object has been achieved by the provision of the pharmaceutical preparations according to the invention containing at least one substituted 2-arylaminoacetic acid compound and/or at least one substituted 2-heteroarylaminoacetic acid compound of the general formula I below.

The present invention accordingly provides a pharmaceutical preparation containing at least one substituted 2-arylaminoacetic acid compound and/or at least one substituted 2-heteroarylaminoacetic acid compound of the general formula I,

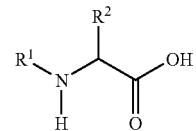

in which $R^1$ denotes a monocyclic aryl or heteroaryl residue, which may be at least monosubstituted and/or fused with an optionally at least monosubstituted monocyclic or polycyclic ring system optionally comprising at least one heteroatom as a ring member, and $R^2$ denotes a monocyclic aryl residue, which may be at least monosubstituted and/or fused with an optionally at least monosubstituted monocyclic or polycyclic ring system optionally comprising at least one heteroatom as a ring member, in each case optionally in the form of one of the pure stereoisomers thereof, in particular enantiomers or diastereomers, the racemates thereof or in the form of a mixture of stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates.

For the purposes of the present invention, a mono- or polycyclic ring system is taken to mean mono- or polycyclic hydrocarbon residues, which may be saturated, unsaturated or aromatic. If a polycyclic ring system is present, it may also comprise in different rings two or more corresponding substructures exhibiting a different degree of saturation. The mono- or polycyclic ring system may optionally also comprise one or more heteroatoms as ring members, wherein the different rings of the polycyclic ring system may comprise identical or different heteroatoms. If a polycyclic ring system is present, the individual rings thereof are preferably fused with one another.

The substituted 2-arylaminoacetic acid compounds and/or substituted 2-heteroarylaminoacetic acid compounds of the general formula I which may preferably be considered for the pharmaceutical preparations according to the invention are those in which the residue $R^1$ denotes a 5- or 6-membered, monocyclic aryl or heteroaryl residue, which may be at least monosubstituted and/or fused with an optionally at least monosubstituted mono-, di- or tricyclic ring system optionally comprising at least one heteroatom as a ring member, wherein the rings of the ring system are in each case 5- to 7-membered, preferably denotes an optionally at least monosubstituted phenyl, naphthyl, furanyl, thiophenyl, pyrrolyl, imidazolyl, pyrazolyl, pyridinyl, pyrimidinyl, quinolinyl or isoquinolinyl residue, particularly preferably denotes a phenyl residue which is unsubstituted or preferably identically substituted in 3,5-position, and $R^2$ has the above-stated meaning, in each case optionally in the form of one of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates.

The substituted 2-arylaminoacetic acid compounds and/or substituted 2-heteroarylaminoacetic acid compounds of the general formula I which may likewise preferably be considered for the pharmaceutical preparations according to the invention are those in which the residue $R^2$ denotes a 5- or 6-membered monocyclic aryl residue, which may be at least monosubstituted and/or fused with an optionally at least monosubstituted mono-, di- or tricyclic ring system optionally comprising at least one heteroatom as a ring member, wherein the rings of the ring system are in each case 5- to 7-membered, preferably denotes a phenyl residue, which may be at least monosubstituted and/or fused with an optionally at least monosubstituted mono- or dicyclic ring system optionally comprising at least one heteroatom as a ring member, wherein the rings of the ring system are in each case 5- or 6-membered, and $R^1$ has the above-stated meaning, in each case optionally in the form of one of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates.

The substituted 2-arylaminoacetic acid compounds and/or substituted 2-heteroarylaminoacetic acid compounds of the general formula I which are particularly preferably used in the pharmaceutical preparations according to the invention are those in which the residue $R^2$ is selected from the group consisting of dibenzofuran-4-yl, dibenzothiophen-4-yl, phenoxathiin-4-yl, thianthren-1-yl and phenyl, in each case unsubstituted or at least monosubstituted, preferably from the group consisting of dibenzofuran-4-yl, dibenzothiophen-4-yl, phenoxathiin-4-yl, thianthren-1-yl, 2-methylsulfanylphenyl, 3-methylsulfanylphenyl and 4-methylsulfanylphenyl, particularly preferably from the group consisting of dibenzofuran-4-yl, dibenzothiophen-4-yl, phenoxathiin-4-yl and thianthren-1-yl, and $R^1$ has the above-stated meaning, in each case optionally in the form of one of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates.

If $R^1$ denotes an at least monosubstituted monocyclic aryl or heteroaryl residue and/or comprises an at least monosubstituted mono- or polycyclic ring system, the corresponding substituents may, in each case mutually independently, preferably be selected from the group consisting of linear or branched, optionally at least monosubstituted, $C_{1-6}$ alkyl optionally attached via an oxygen atom or a sulfur atom, linear or branched, optionally at least monosubstituted $C_{2-6}$ alkenyl, optionally attached via an oxygen atom or a sulfur atom, linear or branched, optionally at least monosubstituted, $C_{2-6}$ alkynyl optionally attached via an oxygen atom or a sulfur atom, optionally at least monosubstituted $C_{3-8}$ cycloalkyl optionally comprising at least one heteroatom, optionally attached via an oxygen atom or a sulfur atom, halogen, OH, SH, CN, optionally at least monosubstituted phenyl, naphthyl, furanyl, thiophenyl, pyrrolyl, imidazolyl, pyrazolyl, pyridinyl, pyrimidinyl, quinolinyl or isoquinolinyl optionally attached via an oxygen atom or a sulfur atom. The substituents may particularly preferably be selected from the group consisting of F, Cl, Br, I, OH, SH, unsubstituted $C_{1-6}$ alkyl, unsubstituted $C_{1-6}$ alkoxy, $C_{1-6}$ perfluoroalkyl, $C_{1-6}$ perfluoroalkoxy, unsubstituted $C_{1-6}$ alkylsulfanyl, $C_{1-6}$ perfluoroalkylsulfanyl, unsubstituted phenylsulfanyl, unsubstituted cyclopentyl and unsubstituted cyclohexyl.

If one of these above-stated substituents is itself mono- or polysubstituted, the substituents thereof may preferably be selected from the group consisting of F, Cl, Br, hydroxy, CN, $CF_3$, $CHF_2$ and $CH_2F$.

If $R^2$ denotes an at least monosubstituted monocyclic aryl residue and/or comprises an at least monosubstituted mono- or polycyclic ring system, the corresponding substituents may, in each case mutually independently, preferably be selected from the group consisting of linear or branched, optionally at least monosubstituted, $C_{1-6}$ alkyl optionally attached via an oxygen atom or a sulfur atom, linear or branched, optionally at least monosubstituted $C_{2-6}$ alkenyl, optionally attached via an oxygen atom or a sulfur atom, linear or branched, optionally at least monosubstituted, $C_{2-6}$ alkynyl optionally attached via an oxygen atom or a sulfur atom, optionally at least monosubstituted $C_{3-8}$ cycloalkyl optionally comprising at least one heteroatom, optionally attached via an oxygen atom or a sulfur atom, halogen, OH, SH, optionally at least monosubstituted phenyl, naphthyl, furanyl, thiophenyl, pyrrolyl, imidazolyl, pyrazolyl, pyridinyl, pyrimidinyl, quinolinyl or isoquinolinyl optionally attached via an oxygen atom or a sulfur atom. The substituents may particularly preferably be selected from the group consisting of F, Cl, Br, I, OH, SH, unsubstituted $C_{1-6}$ alkyl, unsubstituted $C_{1-6}$ alkoxy, $C_{1-6}$ perfluoroalkyl, $C_{1-6}$ perfluoroalkoxy, unsubstituted $C_{1-6}$ alkylsulfanyl, $C_{1-6}$ perfluoroalkylsulfanyl, unsubstituted phenylsulfanyl, unsubstituted cyclopentyl and unsubstituted cyclohexyl.

If one of these above-stated substituents is itself mono- or polysubstituted, the substituents thereof may preferably be selected from the group consisting of F, Cl, Br, hydroxy, CN, $CF_3$, $CHF_2$ and $CH_2F$.

If one or more residues $R^1$ and/or $R^2$ denote(s) one of the above-stated residues, which comprise one or more heteroatoms, these heteroatoms may, unless otherwise stated, preferably be selected from the group consisting of nitrogen, oxygen and sulfur. The heteroatoms are particularly preferably oxygen and/or sulfur.

The pharmaceutical preparations according to the invention very particularly preferably contain at least one substituted 2-arylaminoacetic acid compound and/or at least one substituted 2-heteroarylaminoacetic acid compound of the general formula I selected from the group consisting of: (dibenzofuran-4-yl)-(3,5-dichlorophenylamino)acetic acid, (dibenzothiophen-4-yl)-(3,5-dichlorophenylamino)acetic acid, (3,5-dichlorophenylamino)-(phenoxathiin-4-yl)acetic acid, (3,5-dichlorophenylamino)-(thianthren-1-yl)acetic acid, (3,5-dichlorophenylamino)-(2-methylsulfanylphenyl) acetic acid, (3,5-dichlorophenylamino)-(4-methylsulfanylphenyl)acetic acid and (3,5-bis(trifluoromethyl)phenylamino)-(dibenzothiophen-4-yl)acetic acid, in each case optionally in the form of one of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates.

It has surprisingly been found that the substituted 2-arylaminoacetic acid compounds and/or the substituted 2-heteroarylaminoacetic acid compounds of the above general formula I exhibit an elevated affinity for the glycineB binding site of the NMDA receptor channel and are suitable as glycineB antagonists on the NMDA receptor complex for regulating the calcium balance of the cells in the transmission of pain and thus inter alia also for regulating the perception of pain.

The pharmaceutical preparations according to the invention containing at least one substituted 2-arylaminoacetic acid compound and/or at least one substituted 2-heteroarylaminoacetic acid compound of the general formula I in particular exhibit marked activity in combatting pain, preferably chronic and/or neuropathic pain.

The pharmaceutical preparations according to the invention containing at least one substituted 2-arylaminoacetic acid compound and/or at least one substituted 2-heteroarylaminoacetic acid compound of the general formula I are moreover suitable for the treatment of anxiety states, inflammatory and/or allergic reactions, depression, abuse of drugs and/or medicines and/or alcohol, gastritis, diarrhoea, urinary incontinence, cardiovascular diseases, respiratory diseases, coughing, mental health conditions, epilepsy, schizophrenia, neurodegenerative diseases, preferably Alzheimer's disease and/or Huntington's chorea and/or Parkinson's disease and/or multiple sclerosis, cerebral ischaemia, cerebral infarcts, psychoses brought about by elevated amino acid levels, strokes, cerebral oedema, hypoxia, anoxia, AIDS dementia, encephalomyelitis, Tourette's syndrome, tinnitus and perinatal asphyxia.

The substituted 2-arylaminoacetic acid compounds and the substituted 2-heteroarylaminoacetic acid compounds used according to the invention may be produced using conventional methods known to the person skilled in the art, such as for example described in U.S. Pat. No. 6,232,467; WO 00/24510; WO 01/55091; N. A. Petasis, L. A. Zavialov, J. Am. Chem. Soc. 119, 445-446 (1997); N. A. Petasis, A. Goodman, I. A. Zavialov, Tetrahedron 53, 16463-16470 (1997), N. A. Petasis, S. Boral, Tetrahedron Lett. 42, 539-542 (2001) and G. S. Currie et al., J. Chem. Soc., Perkin Trans, 1 (2000), 2982-2990. The corresponding descriptions are hereby introduced as a reference and are deemed to be part of the disclosure.

The substituted 2-arylaminoacetic acid compounds or substituted 2-heteroarylaminoacetic acid compounds of the above general formula I used according to the invention are preferably produced by reacting at least one amine of the general formula II

in which $R^1$ has the above-stated meaning, with glyoxylic acid (OHC—COOH), optionally in the form of a hydrate, and at least one boronic acid of the general formula III

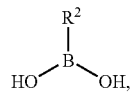

in which $R^2$ has the above-stated meaning, in a suitable reaction medium, preferably in an organic solvent, particularly preferably in methylene chloride or a mixture containing methylene chloride, to yield at least one compound of the general formula I and this is optionally purified and isolated using conventional methods known to the person skilled in the art.

The above-described reaction preferably proceeds at a temperature of 15° C. to 30° C., particularly preferably at a temperature of 20 to 25° C.

The above-described process for the production of compounds of the general formula I used in the pharmaceutical preparation according to the invention has the advantage that the amines used of the general formula II, the glyoxylic acid and the boronic acids of the general formula III are soluble in the reaction medium, but the substituted 2-arylaminoacetic acid compounds and the substituted 2-heteroarylaminoacetic acid compounds of the general formula I in contrast are usually insoluble, such that they may be obtained in pure form by simple filtration and washing with the reaction medium used.

The substituted 2-arylaminoacetic acid compounds and substituted 2-heteroarylaminoacetic acid compounds of the general formula I and corresponding stereoisomers may be obtained using conventional methods known to the person skilled in the art in the form of the physiologically acceptable salts thereof, wherein the pharmaceutical preparations according to the invention may comprise one or more salts of one or more compounds of the general formula I.

If the compounds used according to the invention of the general formula I assume the form of basic salts, these are preferably salts of alkali metals, alkaline earth metals or ammonium salts, particularly preferably sodium, potassium, calcium, magnesium or ammonium salts, wherein ammonium salts are taken to mean not only $[NH_4]^+$ salts but also $[NH_xR_{4-x}]^+$ salts with $R=C_{1-4}$ alkyl and $x=0-3$, very particularly preferably sodium salts.

If the compounds used according to the invention of the general formula I assume the form of acidic salts, these may be obtained, for example, by reaction with an inorganic or organic acid, preferably with hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, cyclohexanesulfamic acid, aspartame, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salts of the compounds of the general formula I used according to the invention are particularly preferred.

The corresponding hydrochloride salts may preferably be obtained by converting the particular substituted 2-arylaminoacetic acid compound and/or substituted 2-heteroarylaminoacetic acid compound of the general formula I and/or corresponding stereoisomers into the corresponding hydrochloride salts by combination of the compounds of the general formula I or corresponding stereoisomers in unprotonated form, dissolved in a suitable organic solvent, such as for example butan-2-one (methyl ethyl ketone), with trimethylsilyl chloride (TMSCl) and water.

The substituted 2-arylaminoacetic acid compounds and/or 2-heteroarylaminoacetic acid compounds of the general formula I and corresponding stereoisomers may optionally be obtained in the form of the solvates thereof, preferably the hydrates thereof, using conventional methods known to the person skilled in the art, as may the corresponding acids, the corresponding bases or the salts of these compounds.

If the substituted 2-arylaminoacetic acid compounds and/or the substituted 2-heteroarylaminoacetic acid compounds of the general formula I are obtained after the production thereof in the form of a mixture of the stereoisomers thereof, preferably in the form of the racemates thereof or other mixtures of their various enantiomers and/or diastereomers, these may be separated and optionally isolated by conventional methods known to the person skilled in the art. Examples which may be mentioned are chromatographic separation methods, in particular liquid chromatography methods at standard pressure or at elevated pressure, preferably MPLC and HPLC methods, and fractional crystallisation methods. Individual enantiomers, for example diastereomeric salts formed by means of HPLC on a chiral phase or by means of crystallisation with chiral acids, for instance (+)-tartaric acid, (−)-tartaric acid or (+)-10-camphorsulfonic acid, may here in particular be separated from one another.

The substituted 2-arylaminoacetic acid compounds and/or 2-heteroarylaminoacetic acid compounds of the general formula I and corresponding stereoisomers as well as in each case the corresponding acids, bases, salts and solvates are toxicologically safe and are therefore suitable as pharmaceutical active ingredients in pharmaceutical preparations.

The present invention also provides the use of at least one substituted 2-arylaminoacetic acid compound and/or at least one substituted 2-heteroarylaminoacetic acid compound of the general formula I for the production of a pharmaceutical preparation for combatting pain, preferably neuropathic and/or chronic pain, for regulating the glycineB binding site on the NMDA receptor complex and for the treatment of anxiety states, inflammatory and/or allergic reactions, depression, the abuse of drugs and/or alcohol and/or medicines, gastritis, diarrhoea, urinary incontinence, cardiovascular diseases, respiratory diseases, coughing, mental health conditions, epilepsy, schizophrenia, neurodegenerative diseases, preferably of Alzheimer's disease and/or Huntington's chorea and/or Parkinson's disease and/or multiple sclerosis, cerebral ischaemia, cerebral infarcts, psychoses brought about by elevated amino acid levels, strokes, cerebral oedema, hypoxia, anoxia, AIDS dementia, encephalomyelitis, Tourette's syndrome, tinnitus and/or perinatal asphyxia.

The pharmaceutical preparations according to the invention may assume the form of liquid, semisolid or solid dosage forms, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally press-moulded into tablets, packaged in capsules or suspended in a liquid, and also be administered as such.

Apart from one or more substituted 2-arylaminoacetic acid compounds and/or one or more substituted 2-heteroarylaminoacetic acid compounds of the general formula I, optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

Substituted 2-arylaminoacetic acid compounds and/or substituted 2-heteroarylaminoacetic acid compounds of the general formula I, optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, in a depot in dissolved form or in a dressing, optionally with the addition of skin penetration promoters, are suitable percutaneous administration preparations.

Orally or percutaneously administrable formulations may also release the particular substituted 2-arylaminoacetic acid compounds and/or the substituted 2-heteroarylaminoacetic acid compounds of the general formula I, optionally in the form of the pure stereoisomers thereof, in particular enantiomers or diastereomers, of the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, in delayed manner.

The quantity the particular substituted 2-arylaminoacetic acid compounds and/or the substituted 2-heteroarylaminoacetic acid compounds of the general formula I, optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, to be administered to patients may vary and is for example dependent on the weight or age of the patient and on the mode of administration, the indication and the severity of the complaint. Conventionally, 0.005 to 500 mg/kg, preferably 0.05 to 5 mg/kg of patient body weight of at least one substituted 2-arylaminoacetic acid compound and/or at least one substituted 2-heteroarylaminoacetic acid compound of the general formula I is administered, optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates.

Pharmacological Methods (a) Receptor Binding Study (GlycineB Binding Site of the NMDA Receptor Channel)

The affinity of the compounds of the general formula I used according to the invention for the glycine binding site of the NMDA receptor channel is determined using brain membrane homogenates (homogenate of cortex and hippocampus area from the brain of male rats, Wistar strain), as for example described in B. M. Baron, B. W. Siegel, B. L. Harrison, R. S. Gross, C. Hawes and P. Towers, Journal of Pharmacology and Experimental Therapeutics, (1996), vol. 279, page 62. The corresponding literature description is hereby introduced as a reference and is deemed to be part of the disclosure.

To this end, the cortex and hippocampus are dissected out of freshly harvested rat brains and homogenised with ice cooling in 5 mmol/l of TRIS-acetate buffer, 0.32 mol/l of sucrose, pH 7.4 (10 ml/g fresh weight) using a Potter homogeniser (Braun/Melsungen, 10 piston strokes at 500 rpm) and then centrifuged for 10 minutes at 1,000 g and 4° C. The first supernatant is collected and the sediment again homogenised with ice cooling with 5 mmol/l of tris-acetate buffer, 0.32 mol/l of sucrose, pH 7.4 (5 ml/g of original fresh weight) with the Potter homogeniser (10 piston strokes at 500 rpm) and centrifuged for 10 minutes at 1,000 g and 4° C. The resultant supernatant is combined with the supernatant from the first centrifugation and centrifuged at 17.000 g for 20 minutes at 4° C. The supernatant after this centrifugation is discarded and the membrane sediment resuspended with 5 mmol/l of TRIS-acetate buffer, pH 8.0 (20 ml/g of original fresh weight) and homogenised with 10 piston strokes at 500 rpm.

The membrane homogenate is then incubated for 1 hour at 4° C. and centrifuged for 30 minutes at 50,000 g and 4° C. The supernatant is discarded and the centrifuge tubes containing the membrane sediment are sealed with Parafilm and frozen for 24 hours at −20° C. On the following day, the membrane sediment is thawed and resuspended with ice-cold 5 mmol/l TRIS-acetate buffer, 0,1% saponin (wt./vol.), pH 7.0 (10 ml/g of original fresh weight) and homogenised with 10 piston strokes at 500 rpm and then centrifuged for 20 minutes at 50.000 g and 4° C. The resultant supernatant is discarded and the sediment resuspended in a small volume with 5 mmol/l of TRIS-acetate buffer, pH 7.0 (approx. 2 ml/g of original fresh weight) and again homogenised with 10 piston strokes at 500 rpm. After determination of the protein content, the membrane homogenate is adjusted with 5 mmol/l TRIS-acetate buffer, pH 7.0, to a protein concentration of 10 mg of protein/ml and frozen in aliquots until used for testing.

The receptor binding test is performed by thawing aliquots, diluting them 1:10 with 5 mmol/l TRIS-acetate buffer, pH 7.0, homogenising them with ice-cooling with 10 piston strokes at 500 rpm with the Potter homogeniser (10 piston strokes at 500 rpm) and centrifuging them for 60 minutes at 55,000 g at 4° C. The supernatant is decanted and the membrane sediment adjusted with ice-cold 50 mmol/l TRIS-acetate buffer, pH 7.0, to a protein concentration of 1 mg/ml and again homogenised with 10 piston strokes at 500 rpm and kept in suspension in an ice bath with stirring on a magnetic stirrer. This membrane homogenate is used in the receptor binding test in a quantity of 100 ▯l per 1 ml batch (0.1 mg of protein/ml in the final batch). In the binding test, the buffer used was 50 mmol/l TRIS-acetate buffer, pH 7.0, and the radioactive ligand was 1 mmol/l of ($^3$H)-MDL 105.519 (B. M. Baron et al., 1996). The level of nonspecific binding is determined in the presence of 1 mmol/l of glycine.

In further batches, the compounds used according to the invention are added in concentration series and the displacement of the radioactive ligand from its specific binding at the glycine-binding site of the NMDA receptor channel is determined. Each of the triplicate batches is incubated for 120 minutes at 4° C. and then harvested by filtration through glass fibre filter mats (GF/B) in order to determine the radioactivity bound to the membrane homogenate. The radioactivity retained on the glass fibre filters is measured, after addition of scintillating material (Ready Protein, Beckmann Coulter GmbH, Krefeld, Germany) in the β-counter (Packard TRI-CARB Liquid Scintillation Analyzer 2000 CA, Packard Instrument, Meriden, Conn. 06450, USA).

(b) Formaldehyde Test (Mouse)

The investigations for determining the antinociceptive action of the substituted 2-arylaminoacetic acid compounds and/or substituted 2-heteroarylaminoacetic acid compounds of the above general formula I used according to the invention are carried out by the formaldehyde test on male albino mice (NMRI, 25-35 g, Iffa, Credo, Belgium).

In the formaldehyde test, a distinction is drawn between the first (early) phase (0-15 min after formaldehyde injection) and the second (late) phase (15-60 min after formaldehyde injection) (D. Dubuisson et al., Pain, vol. 4, pp. 161-174 (1977)). The early phase, being a direct response to the formaldehyde injection, is considered to be a model of acute pain, while the late phase is considered to be a model of persistent (chronic) pain (T. J. Coderre et al., Pain, vol. 52, pp. 259-285 (1993)). The corresponding literature descriptions are hereby introduced as a reference and are deemed to be part of the disclosure.

The compounds used according to the invention of the general formula I are investigated in the second phase of the formaldehyde test in order to obtain information regarding the action of the substances in chronic/inflammatory pain.

A nociceptive reaction is induced in the freely mobile test animals by a single, subcutaneous formaldehyde injection (20 μl, 1 wt. % aqueous solution) into the dorsal side of the rear hind paw, the reaction being expressed by distinct licking and biting of the affected paw.

For the investigation period in the second (late) phase of the formaldehyde test, nociceptive behaviour is continuously recorded by observing the animals. Pain behaviour is quantified by summing the seconds for which the animals exhibit licking and biting of the affected paw over the investigation period. After injection of the compounds which are antinociceptively active in the formaldehyde test, the described behaviours of the animals are reduced or even eliminated. In the same manner as in the tests, in which the animals receive an injection of test compound before the formaldehyde, the control animals are injected with vehicle, i.e. solvent (for example 0.9% NaCl solution) before administration of the formaldehyde. The behaviour the animals after administration of the substance (n=10 per compound dose) is compared with a control group (n=10). On the basis of the quantification of the pain behaviour, action in the formaldehyde test is determined as a percentage change of the control. $ED_{50}$ calculations are carried out by regression analysis. The time of administration before the formaldehyde injection was selected as a function of the mode of administration of the compounds used according to the invention (intraperitoneal: 15 min; intravenous: 5 min).

The invention is explained below with reference to Examples. These explanations are given merely by way of illustration and do not restrict the general concept of the invention.

EXAMPLES

The chemicals and solvents used were purchased from conventional suppliers (Acros, Aldrich, Chempur, Fluka, Lancaster and Merck).

The NMR spectra were measured with spectrometers made by Bruker Analytik GmbH, Silberstreifen 4, D-76287 Rheinstetten. The instrument names are as follows: for 300 MHz: Avance DPX 300 MHz, for 600 MHz: Avance DRX 600 MHz.

The ESI mass spectra were measured with a Finnigan LCQ model instrument made by Thermoquest (Analytische Systeme GmbH, Boschring 12, D-63329 Egelsbach) and evaluated with Xcalibur software.

General Synthesis Method for the Production of the Optionally Substituted 2-arylaminoacetic Acid Compounds and/or Optionally Substituted 2-heteroarylaminoacetic Acid Compounds of the General Formula I used According to the Invention:

10 mmol of glyoxylic acid hydrate were dissolved in 50 ml of dichloromethane, 10 mmol of the particular amine component of the general formula II and 10 mmol of the particular boronic acid component of the general formula III were added with stirring and stirred overnight at room temperature (approx. 20° C.-25° C.). The precipitated reaction product was removed by suction filtration, washed with a little cold dichloromethane and then dried under a high vacuum. Colourless solids were obtained.

Table 1 below shows the particular compound of the general formula I produced, together with the components of the general formulae II and III used for the production thereof.

Example 1

(Dibenzofuran-4-yl)-(3,5-dichlorophenylamino)acetic acid

Yield: 3.86 g (100% of theoretical)

$^1$H-NMR (d$_6$-DMSO$_{ext.}$): δ=5.69 ppm (d, 1H, α-CH); 6.62 ppm (s, 1H, aryl-H); 6.73 ppm (s, 2H, 2×aryl-H); 7.08 ppm (d, 1H, α-NH); 7.43 ppm (m, 2H, 2×aryl-H); 7.56 ppm (m, 2H, 2×aryl-H); 7.77 ppm (d, 1H, J=8.3 Hz, aryl-H); 8.12 ppm (d, 1H, J=7.6 Hz, aryl-H); 8.16 ppm (d, 1H, J=7.6 Hz, aryl-H); 13.22 ppm (s (wide), 1H, CO$_2$H).

ESI-MS: molar mass (calculated for C$_{20}$H$_{13}$Cl$_2$NO$_3$): 386.20 g/mol

Measured (positive mode): 385.9 (MH$^+$); 340.1 (M-CO$_2$).
Measured (negative mode): 383.9 (M-H); 340.3 (M-CO$_2$), Example 2

(Dibenzothiophen-4-yl)-(3,5-dichlorophenylamino)acetic acid

Yield: 4.02 g (100% of theoretical)

$^1$H-NMR (d$_6$-DMSO$_{ext.}$): δ=5.44 ppm (d, 1H, α-CH); 6.60 ppm (s, 1H, aryl-H); 6.70 ppm (s, 2H, 2×aryl-H); 7.11 ppm (d, 1H, □-NH); 7.50 ppm (m, 2H, 2×aryl-H); 7.57 ppm (m, 1H, aryl-H); 7.67 ppm (m, 1H, aryl-H); 8.03 ppm (m, 1H, aryl-H); 8.38 ppm (m, 2H, 2×aryl-H); 13.38 ppm (s (wide), 1H, CO$_2$H).

ESI-MS: molar mass (calculated for C$_{20}$H$_{13}$Cl$_2$NO$_2$S): 402.30 g/mol

Measured (positive mode): 401.8 (MH$^+$); 356.1 (M-CO$_2$).
Measured (negative mode): 399.9 (M-H); 356.3 (M-CO$_2$).

Example 3

(3,5-Dichlorophenylamino)-(phenoxathiin-4-yl)acetic acid

Yield: 1.07 g (25.4% of theoretical)

$^1$H-NMR (d$_6$-DMSO$_{ext.}$): δ=5.60 ppm (d, 1H, α-CH); 6.60 ppm (s, 1H, aryl-H); 6.71 ppm (s, 2H, aryl-H); 6.95 ppm (d,

TABLE 1

| Example compound | Amine component of the general formula II | Boronic acid component of the general formula III |
|---|---|---|
| Example 1: (Dibenzofuran-4-yl)-(3,5-dichlorophenylamino)acetic acid | 3,5-dichlorophenylamine | dibenzofuran-4-yl-boronic acid |
| Example. 2: (Dibenzothiophen-4-yl)-(3,5-dichlorophenylamino)acetic acid | 3,5-dichlorophenylamine | dibenzothiophen-4-yl-boronic acid |
| Example 3: (3,5-Dichlorophenylamino)-(phenoxathiin-4-yl)acetic acid | 3,5-dichlorophenylamine | phenoxathiin-4-yl-boronic acid |
| Example 4: (3,5-Dichlorophenylamino)-(thianthren-1-yl)acetic acid | 3,5-dichlorophenylamine | thianthren-1-yl-boronic acid |
| Example 5: (3,5-Dichlorophenylamino)-(2-methylsulfanylphenyl)acetic acid | 3,5-dichlorophenylamine | 2-methylsulfanyl-phenylboronic acid |
| Example 6: (3,5-Dichlorophenylamino)-(4-methylsulfanylphenyl)acetic acid | 3,5-dichlorophenylamine | 4-methylsulfanyl-phenylboronic acid |
| Example 7: (3,5-Bis(trifluoromethyl)-phenylamino)-(dibenzothiophen-4-yl)acetic acid | 3,5-bis(trifluoromethyl)phenylamine | dibenzothiophen-4-yl-boronic acid |

1H, a-NH); 7.13 ppm (m, 2H, aryl-H); 7.25 ppm (m, 1H, aryl-H); 7.28-74.0 ppm (m, 5H, aryl-H).

ESI-MS: molar mass (calculated for $C_{20}H_{13}Cl_2NO_3S$): 414.00 g/mol

Measured (positive mode): 417.8 ($MH^+$).

Measured (negative mode): 416.1 (M-H); 372.4 ($M-CO_2$).

Example 4

(3,5-Dichlorophenylamino)-(thianthren-1-yl)acetic acid

Yield: 4.17 g (96% of theoretical)

$^1$H-NMR ($d_6$-$DMSO_{ext.}$): δ=5.70 ppm (d, 1H, α-CH); 6.65 ppm (s, 2H, aryl-H); 7.25 ppm (d, 1H, α-NH); 7.30-7.50 ppm (m, 3H, aryl-H); 7.55-7.70 ppm (m, 2H, aryl-H); 7.75 ppm (m, 1H, aryl-H); 13.40 ppm (s (wide), 1H, $CO_2H$).

ESI-MS: molar mass (calculated for $C_{20}H_{13}Cl_2NO_2S_2$): 431.00 g/mol

Measured (positive mode): 433.8 ($MH^+$).

Measured (negative mode): 434.0 (M-H); 388.3 ($M-CO_2$).

Example 5

(3.5-Dichlorophenylamino)-(2-methylsulfanylphenyl)acetic acid

Yield: 3.27 g (95.5% of theoretical)

$^1$H-NMR ($d_6$-$DMSO_{ext.}$): δ=2.55 ppm (s, 3H, $SCH_3$); 5.45 ppm (d, 1H, J=6.8 Hz, α-CH); 6.60 ppm (m, 3H, 3×aryl-H); 7.03 ppm (d, 1H, J=6.8 Hz, α-NH); 7.21 ppm (t, 1H, J=6.8 Hz, aryl-H); 7.35 ppm (m, 2H, J=7.5 Hz, 2×aryl-H); 7.46 ppm (d, 1H, J=7.6 Hz, aryl-H); 13.11 ppm (s (wide), 1H, $CO_2H$).

ESI-MS: molar mass (calculated for $C_{15}H_{13}Cl_2NO_2S$): 342.25 g/mol

Measured (positive mode): 341.9 ($MH^+$),

Measured (negative mode): 340.0 (M-H); 296.3 ($M-CO_2$).

Example 6

(3,5-Dichlorophenylamino)-(4-methylsulfanylphenyl)acetic acid

Yield: 2.96 g (86.5% of theoretical)

$^1$H-NMR ($d_6$-$DMSO_{ext.}$): δ=2.46 ppm (s, 3H, $SCH_3$); 5.16 ppm (d, 1H, α-CH); 6.60 ppm (s, 1H, aryl-H); 6.67 ppm (s, 2H, aryl-H); 6.90 ppm (d, 1H, α-NH); 7.26 ppm (d, 2H, J=8.3 Hz, aryl-H); 7.42 ppm (d, 2H, J=8.3 Hz, aryl-H); 13.04 ppm (s (wide), 1H, $CO_2H$).

ESI-MS: molar mass (calculated for $C_{15}H_{13}Cl_2NO_2S$): 342.25 g/mol

Measured (negative mode): 340.0 (M-H); 296.3 ($M-CO_2$).

Example 7

(3,5-Bis(trifluoromethyl)phenylamino)-(dibenzothiophen-4-yl)acetic acid

Yield: 4.69 g (100% of theoretical)

$^1$H-NMR ($d_6$-$DMSO_{ext.}$): δ=5.64 ppm (d, 1H, J=5.7 Hz, α-CH); 7.09 ppm (s, 1H, α-NH); 7.31 ppm (s, 2H, 2×aryl-H); 7.49-7.46 ppm (m, 4H, 4×aryl-H); 7.72 ppm (d, 1H, J=7.1 Hz, aryl-H); 8.04 ppm (m, 1H, aryl-H); 8.35-8.41 ppm (m, 2H, 2×aryl-H); 13.49 ppm (s (wide), 1H, $CO_2H$).

ESI-MS: molar mass (calculated for $C_{22}H_{13}F_6NO_2S$): 469.41 g/mol

Measured (negative mode): 468.0 (M-H); 424.5 ($M-CO_2$).

Measured (positive mode): 469.8 ($MH^+$); 424.3 ($M-CO_2$).

General Synthesis Method for the Production of the Corresponding Sodium Salts of the Compounds of the General Formula I:

10 mmol of the particular substituted 2-arylaminoacetic acid compound or the particular substituted 2-heteroarylaminoacetic acid compound of the general formula I were suspended in a little water and 10 mmol 1-normal aqueous sodium hydroxide solution were added. In the event of poor solubility, methanol was added dropwise until dissolution was complete. After 30 minutes' stirring at room temperature (approx. 20-25° C.), the solution was evaporated in a rotary evaporator, the remaining solution was frozen at −60° C. in a mixture of isopropanol/dry ice and freeze-dried. The sodium salts were obtained as colourless solids.

Example 8

(Dibenzofuran-4-yl)-(3-5-dichlorophenylamino)acetic acid, sodium salt

Yield: 3.37 g (82.5% of theoretical)

$^1$H-NMR ($d_6$-$DMSO_{ext.}$): δ=5.64 ppm (d, 1H, α-CH); 6.60 ppm (s, 1H, aryl-H); 6.71 ppm (s, 2H, 2×aryl-H); 7.06 ppm (d, 1H, J=7.6 Hz, α-NH); 7.43 ppm (m, 2H, 2×aryl-H); 7.54 ppm (m, 2H, 2×aryl-H); 7.76 ppm (d, 1H, J=8.3 Hz, aryl-H); 8.10 (d, 1H, J=7.6 Hz, aryl-H); 8.16 ppm (d, 2H, J=7.6 Hz, aryl-H).

Example 9

(Dibenzothiophen-4-yl)-(3,5-dichlorophenylamino)acetic acid, sodium salt

Yield: 4.00 g (94% of theoretical)

$^1$H-NMR ($d_6$-$DMSO_{ext.}$): δ=4.70 ppm (m, 1H, α-CH); 6.45 ppm (s, 1H, aryl-H); 6.49 ppm (s, 2H, 2×aryl-H); 6.82 ppm (m, 1H, α-NH); 7.44 ppm (m, 3H, 3×aryl-H); 7.56 ppm (m, 1H, aryl-H); 7.96 ppm (m, 1H, J=6.8 Hz, aryl-H); 8.16 ppm (d, 1H, J=7.6 Hz, aryl-H).

Example 10

(3,5-Dichlorophenylamino)-(phenoxathiin-4-yl)acetic acid, sodium salt

Yield: 4.32 g (97.7% of theoretical)

$^1$H-NMR ($d_6$-$DMSO_{ext.}$): δ=4.99 ppm (d, 1H, J=4.5 Hz, α-CH); 6.40 ppm (s, 1H, aryl-H); 6.49 ppm (s, 2H, 2×aryl-H); 6.72 ppm (d, 1H, J=5.3 Hz, α-NH); 6.97 ppm (m, 1H, aryl-H); 7.05 ppm (m, 1H, aryl-H); 7.12 ppm (m, 1H, aryl-H), 7.17 ppm (m, 1H, aryl-H); 7.25-7.32 ppm (m, 3H, 3×aryl-H).

ESI-MS: molar mass (calculated for $C_{20}H_{14}Cl_2NNaO_3S$): 443.0 g/mol

Measured (negative mode): 418.0 (M-H—Na); 372.3 (M-Na—$CO_2$).

Example 11

(3,5-Dichlorophenylamino)-(thianthren-1-yl)acetic acid, sodium salt

Yield: 4.18 g (87.2% of theoretical)

$^1$H-NMR ($d_6$-$DMSO_{ext.}$): δ=5.07 ppm (s, 1H, α-CH); 6.33 ppm (s, 2H, 2×aryl-H); 6.38 ppm (s, 1H, aryl-H); 6.84 ppm (d, 1H, J=46 Hz, α-NH); 7.18 ppm (t, 1H, J=7.6 Hz, aryl-H); 7.30 ppm (d, 1H, J=7.6 Hz, aryl-H); 7.35 ppm (m, 2H, 2×aryl-H); 7.41 ppm (d, 1H, J=7.6 Hz, aryl-H); 7.58 ppm (m, 1H, aryl-H); 7.69 ppm (m, 1H, aryl-H).

ESI-MS: molar mass (calculated for $C_{20}H_{12}Cl_2NNaO_2S_2$): 479.33 g/mol

Measured (negative mode): 433.9 (M-H—Na); 388.4 (M-Na—$CO_2$).

Example 12

(3,5-Dichlorophenylamino)-(2-methylsulfanylphenyl)acetic acid, sodium salt

Yield: 3.56 g (97.9% of theoretical)

$^1$H-NMR (d$_6$-DMSO$_{ext.}$): δ=2.55 ppm (s, 3H, SCH$_3$); 4.95 ppm (m, 1H, α-CH); 6.41 ppm (s, 1H, aryl-H); 6.47 ppm (s, 2H, 2×aryl-H); 6.77 ppm (d, 1H, J=5.3 Hz, α-NH); 7.07 ppm (t, 1H, J=7.5 Hz, aryl-H); 7.15 ppm (t, 1H, J=6.8 Hz, aryl-H); 7.28 ppm (d, 1H, J=7.6 Hz, aryl-H); 7.36 ppm (d, 1H, J=7.5 Hz, aryl-H).

Example 13

(3,5-Dichlorophenylamino)-(4-methylsulfanylphenyl)acetic acid, sodium salt

Yield: 3.47 g (95.4% of theoretical)

$^1$H-NMR (d$_6$-DMSO$_{ext.}$): δ=2.43 ppm (s, 3H, SCH$_3$); 4.44 ppm (d, 1H, J=4.59 Hz, α-CH); 6.46 ppm (m, 3H, 3×aryl-H); 6.64 ppm (d, 1H, J=5.3 Hz, α-NH); 7.14 ppm (d, 2H, J=8.3 Hz, aryl-H); 7.34 ppm (d, 2H, J=8.4 Hz, aryl-H).

Example 14

(3,5-Bis(trifluoromethyl)phenylamino)-(dibenzothiophen-4-yl)acetic acid, sodium salt Yield: 4.91 g (100% of theoretical)

$^1$H-NMR (d$_6$-DMSO$_{ext.}$): δ=4.74 ppm (s, 1H, α-CH); 6.88 ppm (s, 1H, aryl-H); 7.07 ppm (s (wide), 2H, 2×aryl-H); 7.25 ppm (d, 1H, J=3.7 Hz, α-NH); 7.45 ppm (m, 3H, 3×aryl-H); 7.57 ppm (d, 1H, J=7.6 Hz, aryl-H); 7.97 ppm (d, 1H, J=6.8 Hz, aryl-H); 8.16 ppm (d, 1H, J=7.5 Hz, aryl-H); 8.28 ppm (s, 1H, aryl-H).

ESI-MS: molar mass (calculated for C$_{22}$H$_{12}$F$_6$NNaO$_2$S): 491.39 g/mol Measured (negative mode): 467.9 (M-H—Na); 424.3 (M-Na—CO$_2$).

General Synthesis Method for the Production of the Corresponding Hydrochloride Salts of the Compounds of the General Formula I:

10 mmol of the particular substituted 2-arylaminoacetic acid compound or of the particular substituted 2-heteroarylaminoacetic acid compound of the general formula I were dissolved in 20 ml of butanone, cooled in an ice bath under a protective gas atmosphere, for example nitrogen, and 10 mmol of trimethylsilyl chloride and, in a single portion, 10 mmol of water were added. After stirring overnight, the precipitated solid was filtered out, washed with a little butanone and then with diethyl ether. The hydrochloride salts were obtained as colourless solids.

Example 15

(Dibenzofuran-4-yl)-(3,5-dichlorophenylamino)acetic acid, hydrochloride

Yield: 0.93 g (2.2% of theoretical)

$^1$H-NMR (d$_6$-DMSO$_{ext.}$): δ=5.85 ppm (d, 1H, J=4.5 Hz, α-CH); 6.64 ppm (s, 1H, aryl-H); 6.76 ppm (s, 2H, 2×aryl-H); 7.17 ppm (d, 1H, J=8.4 Hz, α-NH); 7.43 ppm (t, 2H, J=7.6 Hz, 2×aryl-H); 7.55 ppm (m, 2H, 2×aryl-H); 7.76 ppm (d, 1H, J=8.3 Hz, aryl-H); 8.13 ppm (d, 1H, J=7.5 Hz, aryl-H); 8.16 ppm (d, 1H, J=7.5 Hz, aryl-H).

ESI-MS: molar mass (calculated for C$_{20}$H$_{14}$Cl$_3$NO$_3$): 422.70 g/mol

Measured (negative mode): 385.9 (M-HCl—H); 340.3 (M-CO$_2$).

Example 16

(Dibenzothiophen-4-yl)-(3,5-dichlorophenylamino)acetic acid, hydrochloride

Yield: 4.35 g (99.1% of theoretical)

$^1$H-NMR (d$_6$-DMSO$_{ext.}$): δ=5.47 ppm (d, 1H, J=4.9 Hz, α-CH); 6.63 ppm (s, 1H, aryl-H); 6.72 ppm (s, 2H, 2×aryl-H); 7.15 ppm (d, 1H, J=5.6 Hz, α-NH); 7.48-7.58 ppm (m, 3H, 3×aryl-H); 7.68 ppm (d, 1H, J=6.8 Hz, aryl-H); 8.04 ppm (m, 1H, aryl-H); 8.36 ppm (m, 2H, 2×aryl-H); 13.41 ppm (s (wide), 1H, CO$_2$H).

Example 17

(Dichlorophenylamino)-(2-methylsulfanylphenyl)acetic acid, hydrochloride

Yield: 2.82 g (74.5% of theoretical)

$^1$H-NMR (d$_6$-DMSO$_{ext.}$): δ=2.54 ppm (s, 3H, SCH$_3$); 5.54 ppm (d, 1H, J=3.7 Hz, α-CH); 6.62 ppm (m, 2H, 2×aryl-H); 6.65 ppm (m, 1H, aryl); 7.13 ppm (d, 1H, J=7.5 Hz, α-NH); 7.22 ppm (t, 1H, J=Hz, 6.7 Hz, aryl-H); 7.34 ppm (m, 1H, aryl-H); 7.46 ppm (d, 1H, J=6.7 Hz, aryl-H).

Example 18

(3,5-Dichlorophenylamino)-(4-methylsulfanylphenyl)acetic acid, hydrochloride

Yield: 2.89 g (76.4% of theoretical)

$^1$H-NMR (d$_6$-DMSO$_{ext.}$): δ=2.46 ppm (s, 3H, SCH$_3$); 5.18 ppm (d, 1H, J=5.6 Hz, α-CH); 6.62 ppm (t, 1H, J=1.9 Hz, aryl-H); 6.68 ppm (s, 2H, 2×aryl-H); 6.93 ppm (d, 1H, J=7.2 Hz, α-NH); 7.26 ppm (d, 2H, J=8.3 Hz, aryl-H); 7.42 ppm (d, 2H, J=8.2 Hz, aryl-H).

Pharmacological Data (a) Receptor Binding Study (GlycineB Binding Site of the NMDA Receptor Channel)

The affinity of the compounds of the general formula I used according to the invention for the glycine binding site of the NMDA receptor channel was determined as described above and stated in Table 2 below as the percentage fraction of the bound radioactive ligand which is displaced from its specific binding at a concentration of 10 μM of the compound of the general formula I to be tested.

The investigated compounds of the general formula I exhibited excellent affinity for the glycine-binding site of the NMDA receptor channel. The values for some selected compounds are shown in Table 2 below.

TABLE 2

| Compound according to Example | Inhibition % |
|---|---|
| 2 | 33 |
| 5 | 26 |
| 6 | 87 |
| 8 | 29 |
| 10 | 38 |
| 11 | 25 |
| 12 | 39 |
| 13 | 83 |

(b) Formaldehyde Test (Mouse)

The analgesic action of the compounds of the general formula I used according to the invention was determined as described above. The compounds investigated in each case exhibited moderate to strong inhibition of the formaldehyde-induced nociception.

The values for some selected compounds are stated in the Table 3 below:

TABLE 3

| Compound according to Example | Inhibition (at dose) |
| --- | --- |
| 6 | 31% (at 46.4 mg/kg) |
| 12 | 66% (at 31.6 mg/kg) |

The forgoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A pharmaceutical formulation comprising at least one substituted 2-arylaminoacetic acid compound corresponding to formula I,

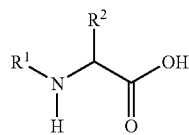

wherein
- $R^1$ denotes a phenyl residue which is identically substituted in the 3,5-position, wherein the substituents are selected from the group consisting of F, Cl, Br, I, OH, SH, unsubstituted $C_{1-6}$ alkyl, unsubstituted $C_{1-6}$ alkoxy, $C_{1-6}$ perfluoroalkyl, $C_{1-6}$ perfluoroalkoxy, unsubstituted $C_{1-6}$ alkylsulfanyl, $C_{1-6}$ perfluoroalkylsulfanyl, unsubstituted phenylsulfanyl, unsubstituted cyclopentyl and unsubstituted cyclohexyl,
- $R^2$ denotes a residue which is selected from the group consisting of dibenzofuran-4-yl, dibenzothiophen-4-yl, phenoxathiin-4-yl, thianthren-1-yl, 2-methylsulfanylphenyl, 3-methylsulfanylphenyl and 4-methylsulfanylphenyl, or an acid, base or a salt thereof, and
a pharmaceutically acceptable adjuvant.

2. The pharmaceutical formulation of claim 1, wherein said compound is present in the form of an acid.

3. The pharmaceutical formulation of claim 1, wherein said compound is present in the form of a base.

4. The pharmaceutical formulation of claim 1, wherein said compound is present in the form of a sodium salt or a hydrochloride salt.

5. The pharmaceutical formulation of claim 1, wherein said compound is present in the form of a pure enantiomer or pure diastereoisomer.

6. The pharmaceutical formulation of claim 1, wherein said compound is present in the form of a mixture of stereoisomers.

7. The pharmaceutical formulation of claim 1, wherein said compound is present in the form of a racemic mixture.

8. The pharmaceutical formulation of claim 1, wherein $R^2$ is selected from the group consisting of dibenzofuran-4-yl, dibenzothiophen-4-yl, phenoxathiin-4-yl and thianthren-1-yl.

9. The pharmaceutical formulation of claim 1, wherein the compound corresponding to formula I is selected from the group consisting of:
- (dibenzofuran-4-yl)-(3,5-dichlorophenylamino)acetic acid,
- (dibenzothiophen-4-yl)-(3,5-dichlorophenylamino)acetic acid,
- (3,5-dichlorophenylamino)-(phenoxathiin-4-yl)acetic acid,
- (3,5-dichlorophenylamino)-(thianthren-1-yl)acetic acid,
- (3,5-dichlorophenylamino)-(2-methylsulfanylphenyl)acetic acid,
- (3,5-dichlorophenylamino)-(4-methylsulfanylphenyl)acetic acid and
- (3,5-bis(trifluoromethyl)phenylamino)-(dibenzothiophen-4-yl)acetic acid.

10. The pharmaceutical formulation of claim 1, wherein said compound is present in an amount pharmaceutically effective for treating pain.

11. The pharmaceutical formulation of claim 1, wherein said compound is present in an amount pharmaceutically effective for treating chronic pain.

12. The pharmaceutical formulation of claim 1, wherein said compound is present in an amount pharmaceutically effective for treating neuropathic pain.

* * * * *